(12) United States Patent
Chin et al.

(10) Patent No.: US 6,343,223 B1
(45) Date of Patent: Jan. 29, 2002

(54) OXIMETER SENSOR WITH OFFSET EMITTERS AND DETECTOR AND HEATING DEVICE

(75) Inventors: Rodney Chin, Oakland; Steven Hobbs, Pasadena, both of CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/483,098

(22) Filed: Jan. 14, 2000

Related U.S. Application Data

(63) Continuation-in-part of application No. 09/447,449, filed on Nov. 22, 1999, and a continuation-in-part of application No. 08/903,120, filed on Jul. 30, 1997.

(51) Int. Cl.$^7$ ................................................. A61B 5/00
(52) U.S. Cl. ........................................ 600/323; 600/334
(58) Field of Search ...................... 600/310, 322–324, 600/334–344

(56) References Cited

U.S. PATENT DOCUMENTS

| | | | | |
|---|---|---|---|---|
| 4,805,623 A | * | 2/1989 | Jobsis | |
| 4,807,631 A | * | 2/1989 | Hersh et al. | |
| 4,819,752 A | * | 4/1989 | Zeliin | |
| 4,822,568 A | * | 4/1989 | Tomita | |
| 4,824,242 A | * | 4/1989 | Frick et al. | |
| 4,869,253 A | * | 9/1989 | Craig, Jr. et al. | |
| 4,869,254 A | * | 9/1989 | Stone et al. | |
| 4,926,867 A | * | 5/1990 | Kanda et al. | |
| 4,928,692 A | * | 5/1990 | Goodman et al. | |
| 5,007,423 A | * | 4/1991 | Branstetter et al. | |
| 5,028,787 A | * | 7/1991 | Rosenthal et al. | |
| 5,048,524 A | * | 9/1991 | Bailey | |
| 5,119,815 A | * | 6/1992 | Chance | |
| 5,213,099 A | * | 5/1993 | Tripp, Jr. | |
| 5,219,400 A | * | 6/1993 | Jacot et al. | |
| 5,246,002 A | * | 9/1993 | Prosser | |
| 5,259,381 A | * | 11/1993 | Cheung et al. | |
| 5,300,769 A | * | 4/1994 | Dahlin et al. | |
| 5,313,940 A | * | 5/1994 | Fuse et al. | |
| 5,348,004 A | * | 9/1994 | Hollub | |
| 5,351,685 A | * | 10/1994 | Potratz | |
| 5,355,882 A | * | 10/1994 | Ukawa et al. | |
| 5,368,224 A | * | 11/1994 | Richardson et al. | |
| 5,372,134 A | * | 12/1994 | Richardson | |
| 5,373,850 A | * | 12/1994 | Kohno et al. | |
| 5,379,238 A | * | 1/1995 | Stark | |
| 5,408,998 A | * | 4/1995 | Mersch | |
| 5,413,101 A | * | 5/1995 | Sugiura | |
| 5,490,523 A | * | 2/1996 | Isaacson et al. | |
| 5,503,148 A | * | 4/1996 | Pologe et al. | |
| 5,551,422 A | * | 9/1996 | Simonsen et al. | |
| 5,551,423 A | * | 9/1996 | Sugiura | |
| 5,596,986 A | * | 1/1997 | Goldfarb | |
| 5,770,454 A | * | 6/1998 | Essenpreis et al. | |
| 5,800,349 A | * | 9/1998 | Isaacson et al. | |
| 5,817,008 A | * | 10/1998 | Rafert et al. | |

* cited by examiner

*Primary Examiner*—Linda C. M. Dvorak
*Assistant Examiner*—David M. Ruddy
(74) *Attorney, Agent, or Firm*—Townsend & Townsend & Crew LLP

(57) ABSTRACT

A method and apparatus for improving blood perfusion by both heating a patient's skin and providing emitters and a detector which are offset from each other. Since the emitters and detector are not directly opposite each other, the light is forced to pass through more blood perfused tissue (with blood perfusion enhanced by heating) to pass from the emitters to the detector. This causes the light emitted by the emitters to pass through more blood-perfused tissue to reach the detector than it would on the direct path through the appendage if the emitters and detector were opposite each other.

26 Claims, 5 Drawing Sheets

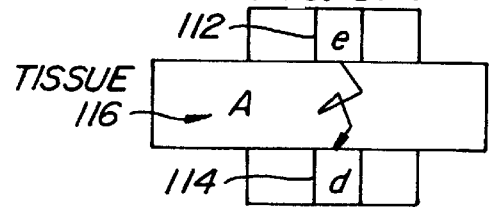
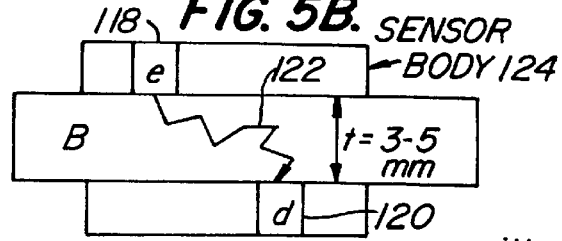
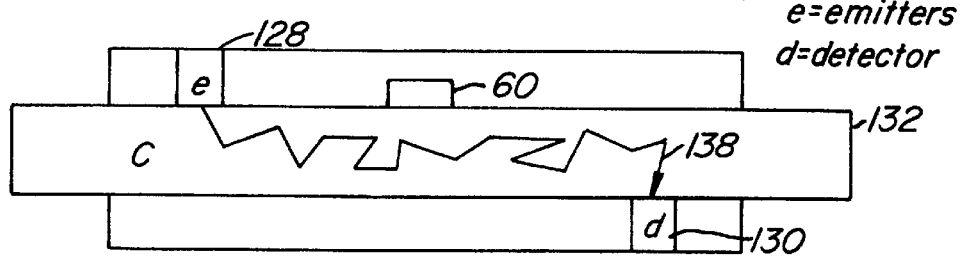
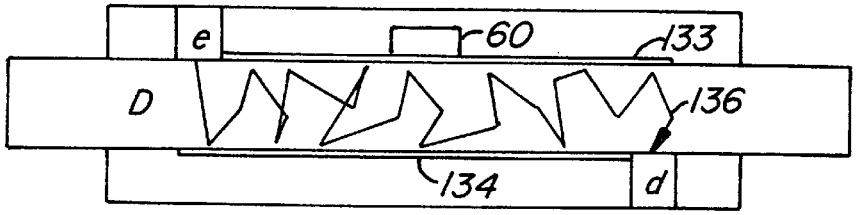
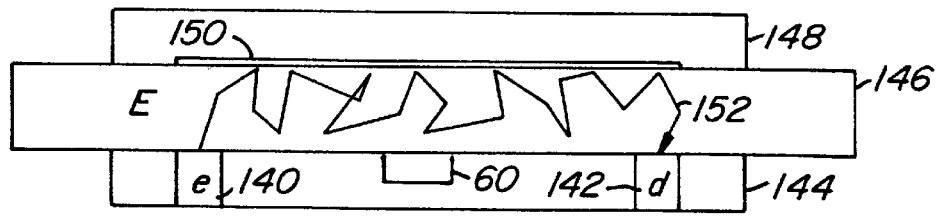
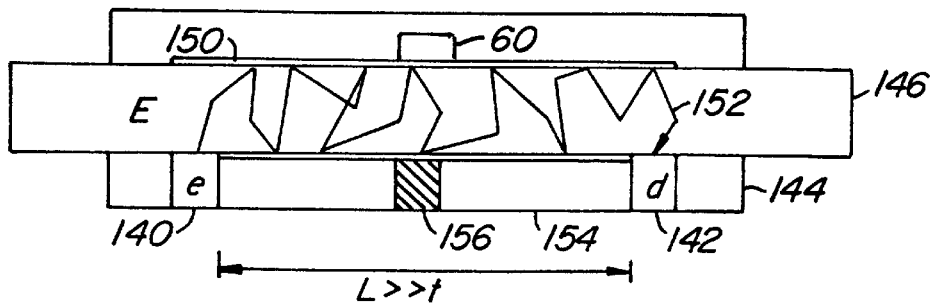
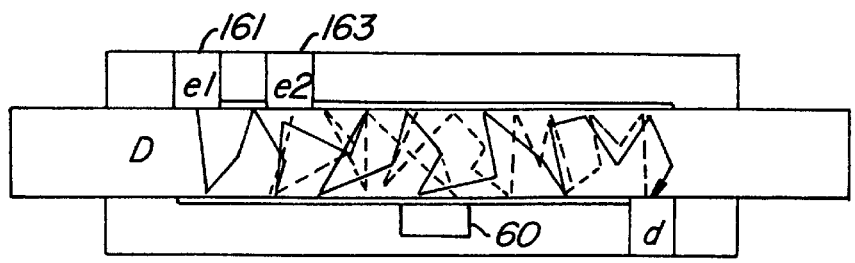

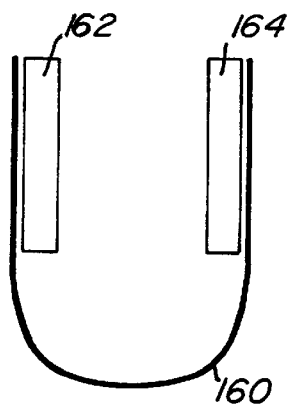 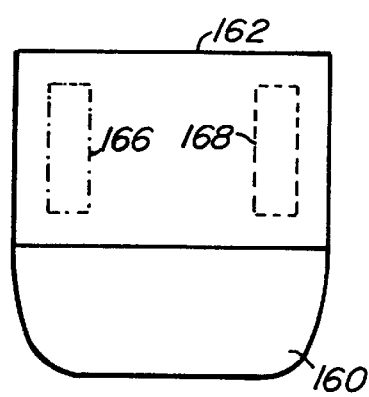 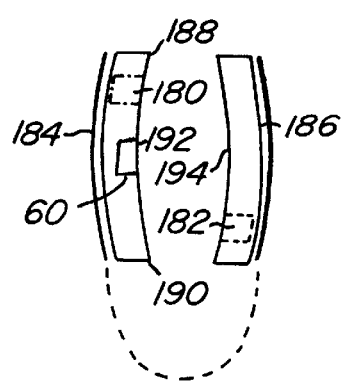
FIG. 6A.  FIG. 6B.  FIG. 8.
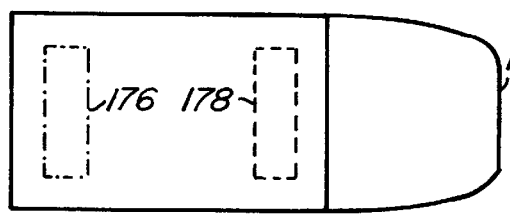 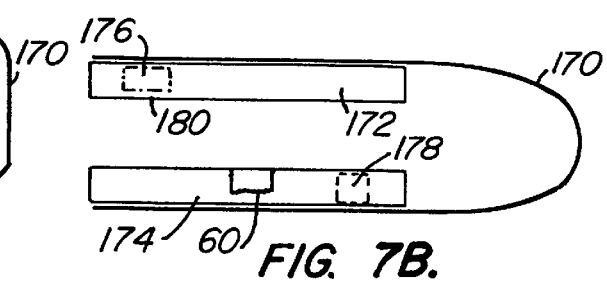
FIG. 7A.  FIG. 7B.
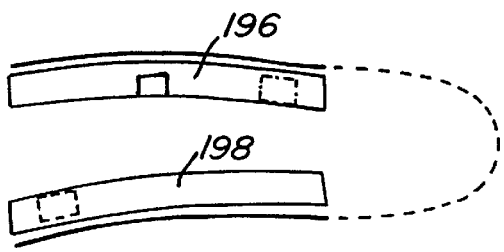 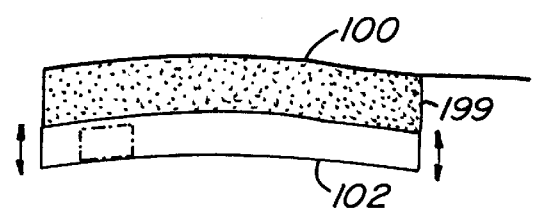
FIG. 9.  FIG. 10.

OXIMETER SENSOR WITH OFFSET EMITTERS AND DETECTOR AND HEATING DEVICE

RELATED APPLICATIONS

This application is a continuation-in-part of applications Ser. No. 08/903,120, filed Jul. 30, 1997, entitled "Oximetry Sensor with Offset Emitters and Detector" and Ser. No. 09/447,449, filed Nov. 22, 1999, entitled "Single Device for Both Heating and Temperature Measurement in an Oximeter Sensor."

BACKGROUND OF THE INVENTION

The present invention relates to oximeter sensors, and in particular oximeter sensors with a heating element to improve perfusion.

Pulse oximetry is typically used to measure various blood characteristics including, but not limited to, the blood-oxygen saturation of hemoglobin in arterial blood, and the rate of blood pulsations corresponding to a heart rate of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Heaters have been used in sensors to improve the perfusion, or amount of blood, adjacent the sensor. This will thus improve the measurement since the light will encounter a larger volume of blood, giving a better signal-to-noise ratio for the oximeter reading.

U.S. Pat. No. 4,926,867 shows a piece of metal used as a heater in an oximeter sensor. A separate thermistor is used to measure the amount of heat so that the heater can be controlled to avoid burning the patient.

U.S. Pat. Nos. 5,299,570 and 4,890,619 both show ultrasonic elements being used for perfusion enhancement.

Because the normal human body core temperature is approximately 37° C., and burning of tissue could take place for temperatures above approximately 42–43° C., a tight range of control of the heating element is required. Another challenge is the heat gradient and delay time between the heating element and the temperature measuring element.

Pulse oximeter sensors are often attached to a digit, or ear. These sites on a patient provide an adequate level of blood perfusion for measuring the oxygenation of the blood hemoglobin. In addition, the distance across these appendages is sufficiently short to allow the detection of transmitted red or infrared light.

One type of sensor is a clothespin-type clip which attaches across the earlobe, with the emitter and detector opposite each other. Such conventional sensors sometime suffer from poor sensitivity and poor calibration or accuracy. This type of sensor often applies pressure which exsanguinates the tissue and alters the blood present leading to accuracy errors.

One type of oximeter sensor will add a diffusing optic to diffuse the light emitted from the light-emitting diodes (LEDs) to cause it to pass through more tissue, and thus more blood. An example of a pulse oximeter sensor using such a diffusing element is shown in U.S. Pat. No. 4,407,290.

One technique for limiting the exsanguination effect is to separate the light emitters and detector from the portion of the sensor which holds it to the appendage and applies the pressure. Examples of sensors where the light emitters and detector avoid the point of pressure are set forth in U.S. Pat. Nos. 5,413,101 and 5,551,422.

Another type of clip-on sensor is marketed by Nonin Medical, Inc. for attaching to an ear. Instead of using a transmission sensor where light is transmitted from an emitter on one side of the ear through the ear to a detector on the other side, a reflectance sensor is used with both the emitter and detector on the same side of the ear. The Nonin medical sensor has spacing between the emitter and the detector of approximately 4 mm, which is similar to the thickness of a typical earlobe. On the opposite side of the ear a reflective surface is provided to reflect the light from the emitter back to the detector.

The typical distance of a standard, bandaid-type reflectance sensor which can attach to the forehead or other part of the body is 6–10 mm. Traditionally, a spacing of this magnitude was felt to be appropriate to ensure that a measurable amount of light could be detected with sufficient pulsatile signal components.

SUMMARY OF THE INVENTION

The present invention provides a method and apparatus for improving blood perfusion by both heating a patient's skin and providing emitters and a detector which are offset from each other. Since the emitters and detector are not directly opposite each other, the light is forced to pass through more blood perfused tissue (with blood perfusion enhanced by heating) to pass from the emitters to the detector. This causes the light emitted by the emitters to pass through more blood-perfused tissue to reach the detector than it would on the direct path through the appendage if the emitters and detector were opposite each other.

In one embodiment, the heater is a thermistor. The thermistor generates controlled heat, and is not just used for sensing the temperature. In an oximetry sensor, the thermistor is located in the vicinity of the light emitter and photodetector to warm the optically-probed tissue region. As heat is dissipated, temperature changes are sensed as resistance changes according to Ohm's law. Active thermal regulation by varying the amount of thermistor current and power can safeguard against burning the tissue while maximizing perfusion. The combination of heating and offset increase the amount of blood that the light from the emitters passes through.

It has been shown recently that general warming of the tissue region increases the amount of blood perfused in the tissue. This increased perfusion substantially strengthens the pulse oximetry signal. Benefits include quick signal acquisition, increased accuracy, and greater tolerance to motion artifact.

In one embodiment, the thermistor is a positive temperature coefficient (PTC) thermistor rather than the more common, negative temperature coefficient (NTC) thermistor. The PTC provides a highly desirable safety feature as poor connections yield a perceived, higher-than-normal resistance indication. As a result, the actual thermistor temperature is regulated at a lower-than-expected temperature, avoiding the chance of burns.

Another advantage of the same thermistor being used for both generating heat and temperature measurement is that there is no thermal gradient between the heating element and the sensing element as in the prior art. This allows for a faster response time, which is critical for maintaining a tight temperature range.

The thermistor's resistance can be conventionally determined either by a two-wire or a four-wire method. The four-wire method is typically used when the connections used in the two-wire method would have resistances that could significantly affect the measurement. In the four-wire method, one pair of wires is used to inject a known current through the thermistor, while the other pair is used to sense the voltage across the thermistor. This enables a highly accurate determination of the thermistor's temperature.

In an alternate embodiment, a simple bridge circuit with a setpoint resistor may be used to automatically bias the thermistor at a particular resistance/temperature. Once the thermistor's desired operating resistance is known from the factory, the appropriate value of the setpoint resistor can be employed in the circuit. This simple circuit could be integrated into the sensor itself or in the remote monitor.

In one offset, the sensor includes at least one reflecting surface for redirecting light back to the blood-perfused tissue in the region of the offset between the emitters and detector. Preferably, the offset distance is at least greater than, and more preferably at least twice as great as, the direct, shortest path through the appendage.

In an alternate embodiment, a reflectance-type sensor is used, with a reflective surface on the opposite side of the appendage. Unlike the prior art, however, the distance between the emitter and detector is greater than, and preferably twice as great as, the shortest, direct distance through the appendage.

For a further understanding of the nature and advantages of the invention, reference should be made to the following description taken in conjunction with the accompanying drawings.

BRIEF DESCRIPTION OF THE DRAWINGS

FIG. 5A is a diagram of a prior art emitter and detector configuration.

FIGS. 5B–5G are diagrams of different embodiments of the configuration of the emitter and detector according to the invention.

FIGS. 6A and 6B are end and side views of an ear sensor according to the invention.

FIGS. 7A and 7B are side and top views of a nostril sensor according to the invention.

FIGS. 8 and 9 are diagrams of alternate embodiments illustrating curves in the sensor.

FIG. 10 is a diagram of a sensor with foam for distributing applied pressure.

DESCRIPTION OF THE SPECIFIC EMBODIMENTS

Figure 1:
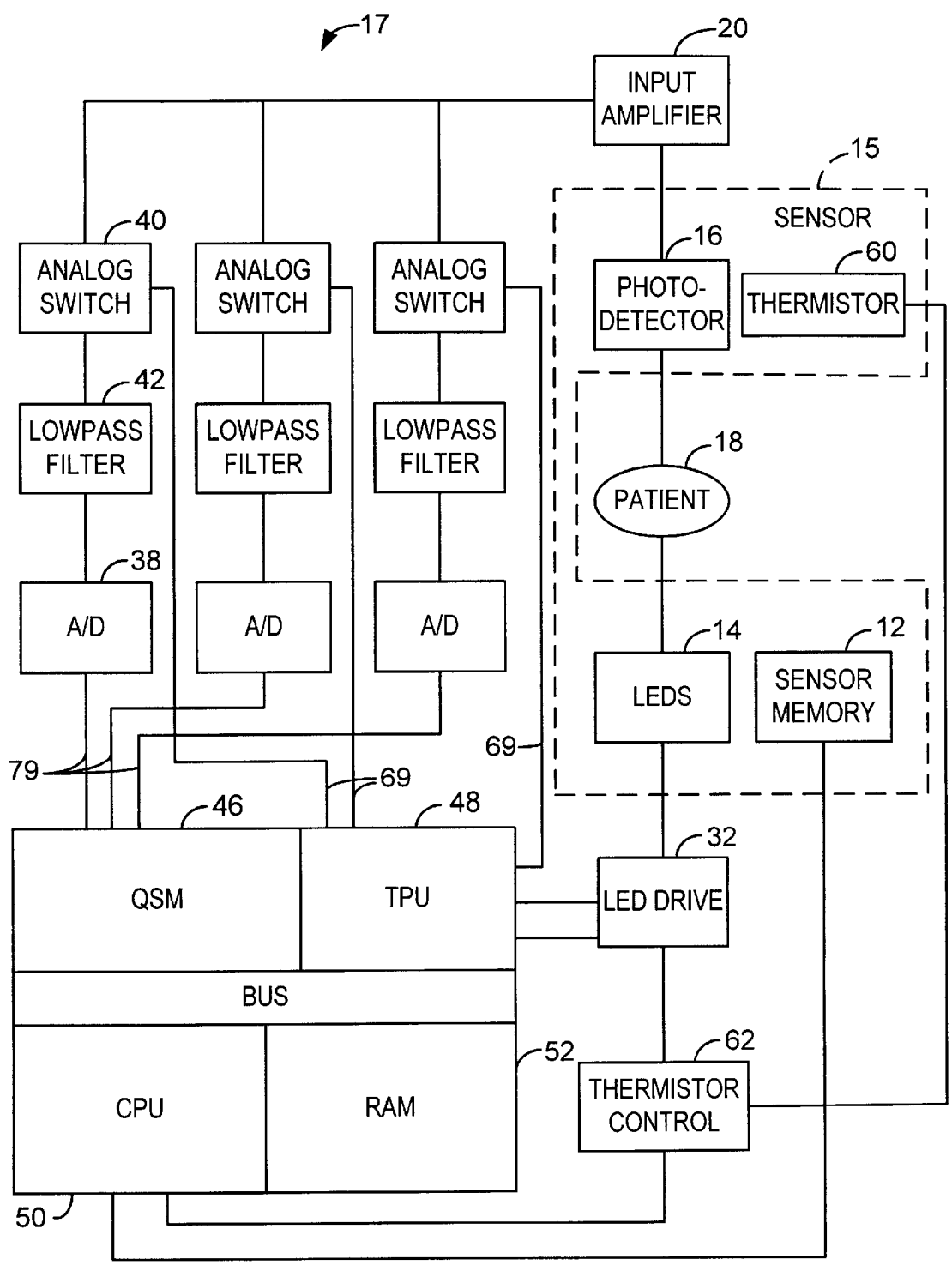
FIG. 1 is a diagram of a pulse oximetry system including the present invention.

FIG. 1 is a block diagram of one preferred embodiment of the invention. FIG. 1 shows a pulse oximeter 17 (or sensor reader) which is connected to a non-invasive sensor 15 attached to patient tissue 18. Light from sensor LEDs 14 passes into the patient tissue 18, and after being transmitted through or reflected from tissue 18, the light is received by photosensor 16. Either two or three LEDs or other light sources can be used depending upon the embodiment of the present invention. The LEDs and photosensor are offset as described in more detail below with respect to FIGS. 5–10. Photosensor 16 converts the received energy into an electrical signal, which is then fed to input amplifier 20.

Light sources other than LEDs can be used. For example, lasers could be used, or a white light source could be used with appropriate wavelength filters either at the transmitting or receiving ends. The light could be delivered to the patient site with fiber optics, with the light source in the sensor or remotely located.

Time Processing Unit (TPU) 48 sends control signals to the LED drive 32, to alternately activate the LEDs, typically in alteration. Again, depending on the embodiment, the drive may control two or any additional desired number of LEDs.

The signal received from input amplifier 20 is passed through three different channels as shown in this embodiment for three different wavelengths. Alternately, two channels for two wavelengths could be used, or N channels for N wavelengths. Each channel includes an analog switch 40, a low pass filter 42, and an analog to digital (A/D) converter 38. Control lines 69 from TPU 48 select the appropriate channel at the time the corresponding LED 14 is being driven, in synchronization. A queued serial module (QSM) 46 receives the digital data from each of the channels via data lines 79. CPU 50 transfers the data from QSM 46 into RAM 52 as QSM 46 periodically fills up. In one embodiment, QSM 46, TPU 48, CPU 50 and RAM 52 are part of one integrated circuit, such as a microcontroller.

A thermistor 60 is shown mounted in sensor 15. Thermistor 60 could be mounted adjacent the photodetector or the LEDs, or nearby. A thermistor control circuit 62 provides the power and current to the thermistor to deliver the desired heat, while measuring the resulting resistance, and thus the temperature. The thermistor can either be a positive temperature coefficient (PTC) or a negative temperature coefficient (NTC) thermistor.

The thermistor is used in a dual capacity to dissipate thermal heat energy and self-monitor its temperature for the safe operation in a "warmed" oximeter sensor.

A positive temperature coefficient (PTC) thermistor is more desirable than a negative temperature coefficient (NTC) thermistor for oximetry/medical applications. For a given voltage source applied to the thermistor, the power dissipation decreases with increasing temperature due to the increased resistance at higher temperatures. Additionally, if there exists connection resistances within the sensor cable and/or connections, the increased series resistance would be perceived by the oximeter as a falsely higher temperature. This is desirable as the oximeter would regulate the sensor at a lower (safe) temperature and avoid the possibility for patient burns. Since PTC thermistors generally have thermal coefficients that are smaller than for NTC, special PTC thermistors may be used. The nonlinear behavior of the switching or nonlinear PTC thermistors is desirable. These are available from Advanced Thermal products, St. Mary's, PA and other sources. The material is processed so the switching temperature is between 40–50° C., generally.

In one embodiment, it is desirable to have a PTC transistor with a phase transition, where the resistance suddenly increases, in the region between 40–50° C. This can be controlled in a number of different ways, such as by appropriate doping of the thermistor material.

In practice, the PTC thermistor is regulated at 39–41° C. This is just slightly above normal (37° C.) core body temperature but below the burn threshold of 42–43° C. It has been shown recently that general warming of the tissue region probed by the oximetry sensor increases localized perfusion and increases the strength of the pulsatile oximetry signal. The benefit of this includes an increase in the acquisition and accuracy of the oximetry measurement and an increase in the tolerance to motion artifact.

An advantage of the same thermistor being used for both generating heat and for measuring it is that there is no thermal gradient between the heating element and the sensing element as in the prior art. This allows for a faster response time, which is critical in maintaining a temperature within a tight range, as required.

Figure 2:
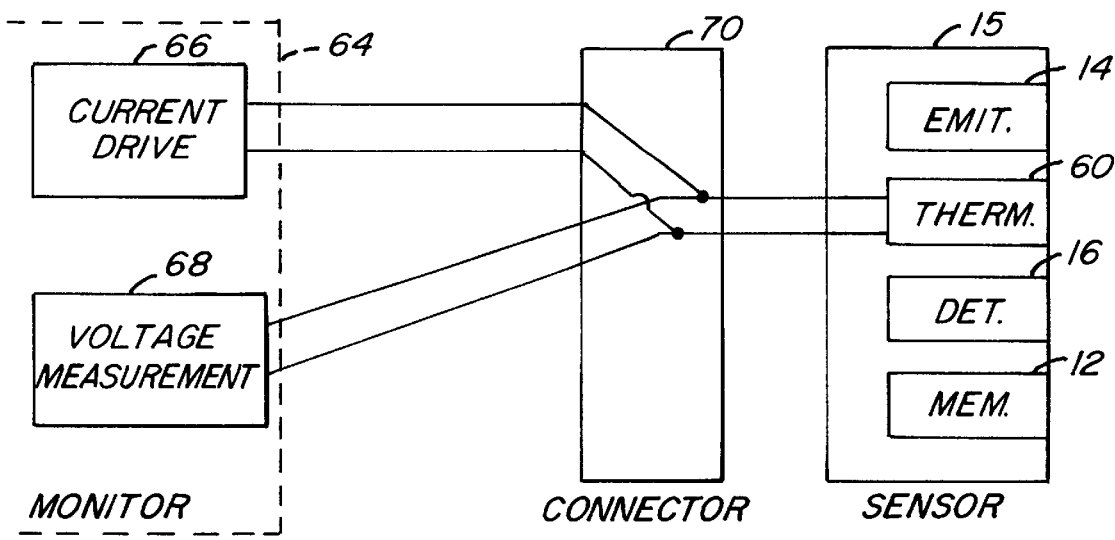
FIG. 2 is a diagram illustrating four-wire measurement in one embodiment of the invention.

FIG. 2 illustrates a four-wire measurement system for a thermistor of the present invention. FIG. 2 shows a monitor 64 with a current drive circuit 66 and a voltage measurement circuit 68. Each are separately connected by two wires to a connector 70 close to sensor 15. From connector 70, the four wires are converted into two wires for connecting to the actual sensor. Alternately, the four wires can extend all the way to thermistor 60.

Current drive circuit 66 is programmable to provide the appropriate amount of current to achieve the desired power dissipation and temperature through thermistor 60. Voltage measurement circuit 68 simultaneously measures the resulting voltage, which will allow the determination of the resistance from the known drive current. By using four wires to a position close to the sensor, the resistance effects of the wiring and any connections are also taken into account.

The other connections in FIG. 2 are not shown in order not to obscure the connections of the thermistor. Memory chip 12 in one embodiment is used to store thermal coefficients of the thermistor or other thermal parameters of the sensor. These parameters can then be read by the oximeter monitor 64 and used by its CPU 50 to determine an appropriate drive current for the thermistor. The temperature control is done in part by the hardware and in part by software in the CPU. The amount of power dissipated in the thermistor is controlled by the resistance measurement, which corresponds to a temperature measurement.

The sensor could be any type of sensor, such as a durable sensor or a disposable sensor. It could attach to any body part, such as the earlobe, finger, etc. The sensor could be a reflectance or a transmittance sensor.

Since commercially available thermistors often vary significantly in their actual resistance value, the thermistors can either be trimmed at the factory, or a precision resistor could be placed in series or in parallel to adjust the resistance to the desired value.

Figure 3:
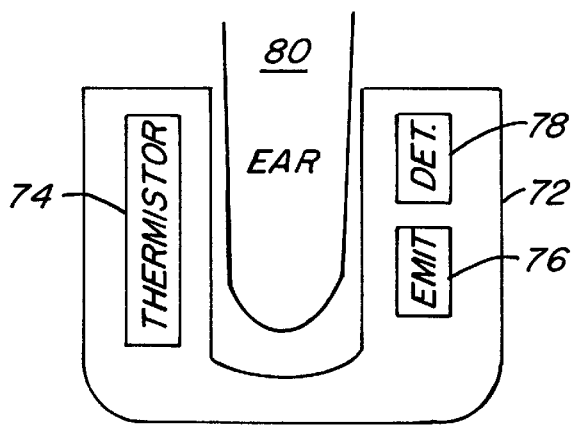
FIG. 3 is a diagram of an embodiment using a large area thermistor and a reflective type oximeter sensor.

In one embodiment, shown in FIG. 3, the sensor 72 uses a single thermistor element 74 with a reflectance geometry. The thermistor is opposite to the reflectance sensor emitter 76 and detector 78. this allows a large warming surface to contact the tissue 80 for the ear sensor.

The thermistor need not directly contact the skin because the thermal loading could be asymmetrically strong to cause a lengthwise thermal gradient and an error in the temperature measurement. The thermistor is in close contact for maximum heat transfer but is somewhat embedded inside the sensor housing. A thin layer between the thermistor and contact surface may act as a buffer to allow a uniform, heat-spreading action.

Figure 4:
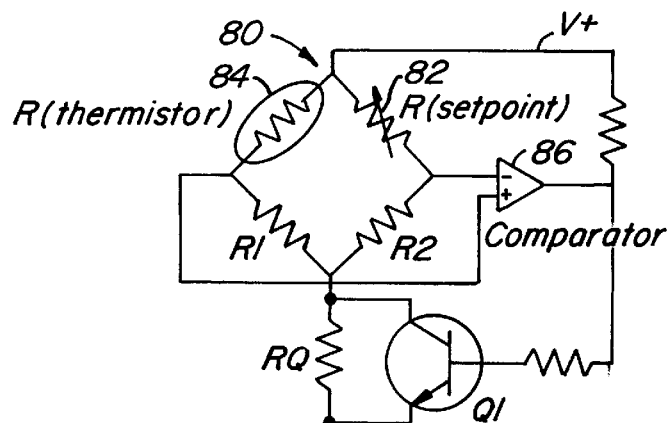
FIG. 4 is a circuit diagram of an embodiment of a bridge circuit for regulating the thermistor temperature.

FIG. 4 is a circuit diagram of an alternate embodiment which allows a thermistor to be set to a desired temperature without intervention by a microprocessor.

A floating resistive bridge circuit 80 can be biased at high or low current. Alternately, this current bias can be made continuously adjustable. The nulling of the bridge signifies when the setpoint temperature has been met. A setpoint resistor 82 is adjusted for the proper setpoint temperature (resistance) of the thermistor 84. When the thermistor's resistance (temperature) is too high, a comparator circuit 86 is switched to cause the bridge to be biased in the low current mode to minimize the current through the thermistor (by turning off transistor Q1, forcing the current through resistor RQ). Conversely, when the thermistor's resistance (temperature) is too low, the comparator circuit is switched to cause the bridge to be biased in the high current mode supplying more current and thus more power to the thermistor (turning on transistor Q1, bypassing resistor RQ). There must be some voltage (current) supplied to the bridge to allow for sensing of the thermistor's resistance for the null measurement of the bridge circuit.

Obviously, a more elaborate thermal regulation circuit could be built. However, it has been found that this circuit works very well with no significant temperature overshoot/undershoot. This is due to the intrinsic self-measurement nature of the system with no thermal delay time between the warming element and the temperature sensor. Typical maximum power dissipation for effective application of a warmed earlobe sensor is less than 0.5 watts per side. With proper heat spreading, the thermistor is efficient at delivering the thermal energy without incurring a large thermal gradient from the thermistor to the tissue. This would give the best tissue temperature and the best performance.

Because of the simplicity of the circuit with few components, it is possible to integrate the whole circuit in the oximetry sensor assembly. The circuit consists of only a few components as shown. The benefit of this would be the requirement of only a single power supply connection and utilizing an existing ground connection. An adapter cable could be used with older instruments to supply the additional supply lead.

FIG. 5A illustrates a prior art configuration in which an emitter 112 is opposite a detector 114 across an earlobe, nostril, digit, or other appendage 116. The present invention provides an offset emitter and sensor to improve upon this arrangement, providing more area for the light to penetrate between emitter and detector. In addition, the figures below show thermistor 60, which provides a heating function to further enhance blood perfusion. Alternately, a simple heater can be substituted for thermistor 60. Also, although clip type sensors are shown below, an adhesive sensor could be used, with reflectance oximetry. Alternately, adhesives could be used to attach a transmissive sensor on an appendage, with adhesives on one or both sides of the appendage.

FIG. 5B illustrates an offset configuration in which an emitter 118 is offset from a detector 120 as can been seen, providing a longer light transmission path 122. Emitter 118 is typically a pair of emitters, an infrared range emitter and a red range emitter, which are mounted in a portion 124 of a sensor probe. Detector 120 is a photodetector which is mounted in a portion 126 of a sensor probe.

FIG. 5C illustrates an alternate embodiment in which emitter 128 is spaced from a detector 130 by an offset distance which is more than twice the width of appendage 132. As can be seen, this provides a much longer transmission path 138.

FIG. 5D illustrates an embodiment similar to FIG. 5C, where a pair of reflectors 133 and 134 have been added. As can be seen, the reflectors 133 and 134 cause the light path 136 in FIG. 5D to be longer than the light path 138 in FIG. 5C. This is due to light which goes across the entire appendage being reflected back in, and then back in from the other surface, bouncing back and forth between the reflectors until it reaches the detector from the emitter. In FIG. 1C, by contrast, the light which reaches the detector from the emitter is substantially the light which moves in a path through the body of the appendage, since light which would hit the edges would typically be absorbed, rather than being reflected.

The reflective surface 133 may be, for instance, a white surface which will reflect both red and infrared light. This will enhance the path length of both red and infrared light. Alternatively, the reflective surface 133 may be "colored" to reflect red light more than infrared light (or vice versa) to compensate for skin pigmentation effects.

FIGS. 5E and 5F show alternate embodiments in which the emitter and detector are on the same side of the appendage in a reflectance configuration. As shown in FIG. 1E, an emitter 140 and a detector 142 are in a portion 144 of a sensor attached to an appendage 146, such as an earlobe. The sensor, which may be a clip-on type sensor, has a second portion 148 opposite portion 144. Portion 148 includes a reflective surface 150. As can be seen, the light path 152 will thus be reflected back from surface 150, providing more light to detector 142 than would be found in a typical reflectance configuration. (Please note that the light path shown in these figures is merely illustrative). The use of reflector 150 allows not only more light to be directed back into the tissue to arrive at detector 142, but allows a larger space between emitter 140 and detector 142. As in FIGS. 5C and 5D, the distance L between the emitter and detector in FIG. 5E is preferably greater than the width t of the appendage, and preferably a value of L which is at least twice t.

FIG. 5F shows an alternate embodiment to that of FIG. 5E in which a second reflector 154 is added between the emitter 140 and detector 142 in portion 144 of the sensor probe. This prevents the light from being absorbed in the body of the sensor 144 between emitter 140 and detector 142 on the same side. A reflector on one side will improve performance over a sensor without such a reflector, while a reflector on both sides would typically give even more enhanced performance. However, even a single reflector provides a significant improvement in the amount of light reaching the detector.

Also shown in FIG. 5F is a shunt barrier 156. Shunt barrier 156 prevents light from shunting directly between emitter 140 and detector 142 through sensor body 144 without passing through appendage 146. Examples of shunt barriers are set forth in commonly-owned copending application entitled SHUNT BARRIER IN PULSE OXIMETER SENSOR, application Ser. No. 08/611,151, filed Mar. 5, 1996.

FIG. 5G shows an alternate embodiment in which two emitters, 161 and 163, have a different offset distance from the detector. This can be used to partially compensate for a difference in absorption of red and infrared.

FIG. 6A shows an end view of one embodiment of an ear clip sensor according to the present invention. Other embodiments are possible, but this embodiment shows a simple, inexpensive, disposable-type sensor. A bent piece of metal 160 holds pads 162 and 164, which contain the light emitters and detector, respectively. Bent metal 160 is springy to provide pressure applying the pads 162, 164 against the earlobe. The pads (162 and 164) are rigid since the earlobe conforms easily. Preferably, slowly deformable spring material is used, which is an assembly which provides the gripping action but has a damping component which prevents quick movements. (e.g., metal sheet as the spring with a rubber coating of laminate).

In the side view of FIG. 6B, pad 162 is shown, along with the position of an emitter 166. Shown in phantom is the position on the other pad where detector 168 would be located.

FIGS. 7A and 7B show a similar configuration for a nostril sensor, which is basically more slender and narrow. As shown in FIG. 7B, a bent metal 170 provides the springiness for pads 172 and 174. Pad 172 includes an emitter 176, while pad 174 includes a detector 178. Also shown is an optional optical diffuser 180 for diffusing the light from emitter 176, which causes a further spreading or mixing of light and may enhance the amount of tissue penetrated in some instances.

FIG. 7A shows a side view with the relative position of emitter 176 and detector 178 shown in phantom.

FIG. 8 illustrates an exaggerated view of the construction of one embodiment of the sensor of FIGS. 6A, 6B, 7A and 7B. In the view of FIG. 8, an emitter 180 and detector 182 are shown.

Emitter 180 is mounted on the edge of a curved portion 184 of one end of the sensor, while detector 182 is mounted near the end of a curved portion 186 on the other side of the sensor. The curvature in FIG. 8 would range from zero (no curvature) to less than 15% depth of offset distance or to less than 30% depth of offset distance. These curved portions ensure that less pressure will be applied to the appendage in-between the emitter and detector. Instead, more pressure is applied, for instance, to points 188 and 190, which are outside of the region in-between the emitter and detector. Thus, this configuration reduces the exsanguination of the tissue in-between the emitter and detector. It is desirable that some pressure is applied throughout to reduce the amount of venous pooling in the tissue.

Preferably, the spring force of the metal clip in the embodiments of FIGS. 6–10 has sufficient pressure so that it exceeds the typical venous pressure of a patient, but does not exceed the diastolic arterial pressure. The signal received by the detector will include both a DC component and an AC component. The AC and DC components are monitored to determine variations in the oxygen saturation. By having a pressure greater than the venous pressure, contributions to the AC waveform from the venous blood are limited, thus enhancing the sensitivity to variations in the arterial blood pressure. Since the pressure of the clip is less than that of the arterial pressure, it does not inhibit the arterial AC signal significantly.

The pressure applied to the spring is such that the pressure exerted on the tissue is equal to the force applied by the spring divided by the contact area to the tissue. Since the system is in steady state, the compressed tissue will be at a minimum pressure exerted by the contact surfaces.

Typical venous pressure, diastolic and systolic arterial pressures are <10–35 mmHg, 80 mmHg, and 120 mmHg, respectively. Functionally, these vary due to the location of the vascular bed and the patient's condition. Low arterial diastolic blood pressure (~30 mmHg) may occur in sick patients. The sensor would/could be adjusted for an average pressure of 15–30 mmHg. It is more desirable to be a little low. Removal of most venous pooling would occur with light to moderate pressure (~15 mmHg). This would give the most enhancement of the pulse modulation by removing unnecessary DC (non-pulsatile) absorption by the blood.

The sensor's pressure may be adjusted by mechanical means to optimize for the best pulse modulation.

In a preferred embodiment, adhesives 192 and 194 are applied to the interior surface of the clip sensor in FIG. 8 to enhance the securing of the sensor to the appendage. Preferably, this is done in combination with a slight curve of the sensor (which is exaggerated in FIG. 8). The use of an adhesive improves the contact of the sensor to the appendage, and limits the susceptibility to motion artifact which might vary the distance or degree of contact between the sensor and the appendage. In addition, due to the curved shape, the likelihood of a gap between the sensor body and the skin is avoided. If the adhesive is thin enough or contains a black barrier segment, it will not shunt appreciably. Such an adhesive can also be used in the sensor configurations of FIGS. 6, 7 and 9. The good contact provided by the adhesive also provides for better thermal conductance.

FIG. 9 illustrates a sensor with concave and convex surfaces 196 and 198. The particular curvature can be matched to the desired patient site. FIG. 10 illustrates the addition of a foam 199 between a sensor spring 100 and a pad 102. Foam 199 can help distribute the pressure from the spring.

Figure 11:
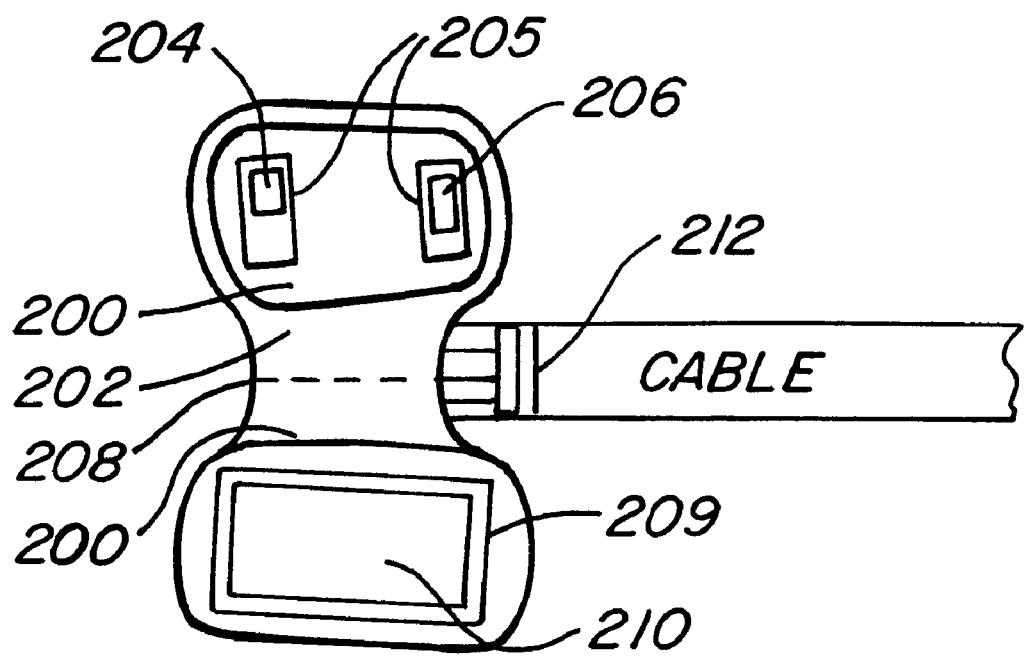
FIG. 11 is a diagram of an adhesive reflectance sensor with a thermistor.

FIG. 11 illustrates an embodiment of a reflectance sensor mounted with an adhesive. The sensor has an adhesive layer 200, which is bonded to an underlying substrate 202. Substrate 202 may be a polyester strip, for example. Emitter 204 and photodetector 206 are mounted to be applied to a first side of an ear, with the sensor folding around the ear near line 208. An opening 205 allows light from the emitter to reach the ear, and a similar opening is used for the photodetector. These openings may optionally be covered with a transparent layer. The sensor wraps around the ear, with the adhesive holding the part with a thermistor 210 on a second side of the ear, opposite the emitter and photodetector. An opening 209 is shown for allowing the thermistor direct contact with the adhesive layer, but this may optionally be eliminated, with thermal contact being provided through both flexible substrate 202 and adhesive layer 200. Alternately, the thermistor could be on the same side of the ear, and/or the entire sensor could be mounted on the same side of the ear. The adhesive 200 is a thermally conductive material. It both avoids direct contact of thermistor 210 with the ear, and provides good heat conduction between the thermistor and the ear.

The substrate 202 is shown folded over on itself, with the electrical components and connecting lines inside. The connecting lines extend to contacts 212, which can be coupled to an oximeter monitor with an appropriate connector. More details on such a flex sensor may be seen in U.S. Pat. No. 5,469,845, issued Nov. 28, 1995.

The present invention provides a number of advantages. The cardiac pulse modulation or AC portion of the detected signal, has been observed in experiments to be increased by greater than three times (providing greater than 1% IR modulation of the DC signal at 100% SpO2). This increased AC cardiac signal level is believed to be due to the longer absorption path length. The increased AC cardiac signal amplitude allows it to be more easily processed by the oximeter electronics and software. In addition, the increased AC cardiac modulation level limits the sensor's susceptibility to noise due to either motion artifact or EMI interference.

The present invention also provides more stable DC levels. The path length is dominated by the offset distance rather than the tissue thickness since the offset distance is much greater. This offset distance for any one particular sensor is consistent from patient to patient. In addition, the increased distance between the emitter and detector limits the amount of direct optical shunting through the tissue, thus further limiting the corrupting effect on the DC level.

As will be understood by those of skill in the art, the present invention may be embodied in other specific forms without departing from the essential characteristics thereof. For example, the thermistor could be placed at any location on the sensor, and some or all of the monitoring or drive circuit could be located on the sensor, on an adapter or connector, or in a remote monitor. Accordingly, the foregoing description is intended to be illustrative, but not limiting, of the scope of the invention which is set forth in the following claims.

What is claimed is:

1. An oximeter sensor comprising:
   a light emitter mounted on a first side of a tissue region of a patient;
   a light detector mounted on a second side of said tissue region of said patient;
   a heating device, controllable to both heat said patient and also measure the temperature of said tissue region, mounted proximate at least one of said light emitter and said light detector; and
   an attachment structure configured to attach said sensor to said tissue region so that said detector is offset from a shortest path through said tissue region from said emitter.

2. The sensor of claim 1 wherein said heating device is a thermistor.

3. The sensor of claim 2 wherein said thermistor is a positive temperature coefficient thermistor.

4. The sensor of claim 2 wherein said thermistor is a switching thermistor.

5. The sensor of claim 4 wherein said thermistor switches at a temperature between 30 and 55 degrees centigrade.

6. The sensor of claim 2 further comprising four wires connected to said thermistor for use in a four wire measurement technique.

7. The sensor of claim 1 further comprising a memory storing at least one calibration value corresponding to a characteristic of said device.

8. The oximeter sensor of claim 1 further comprising:
   a first diffuse or specular reflective surface mounted to attach to said tissue region in a region of said offset.

9. The oximeter sensor of claim 8 wherein said first reflective surface only partially covers said offset region.

10. The oximeter sensor of claim 8 wherein said reflective surface comprises a partially reflective black and white pattern.

11. The oximeter sensor of claim 8 wherein said reflective surface reflects different amounts of light at each wavelength emitted by the emitter.

12. The oximeter sensor of claim 8 further comprising a second reflective surface mounted to said tissue region on an opposite side from said first reflective surface in a region of said offset.

13. The oximeter sensor of claim 1 wherein said offset is greater than said shortest path through said tissue region.

14. The oximeter sensor of claim 1 wherein said offset is more than twice said shortest path.

15. The oximeter sensor of claim 1 wherein said attachment structure comprises a spring loaded U-shaped metal or plastic clip, said first member being a first end of said clip, and said second member being a second end of said clip.

16. The oximeter sensor of claim 15 wherein said first and second members and said attachment structure comprise a flexible substrate, and further comprising an adhesive for attaching said flexible substrate to said tissue region.

17. The oximeter sensor of claim 15 wherein said attachment structure is configured to apply a pressure to said tissue region between said emitter and said detector which is between a venous and a diastolic arterial pressure of said patient in said tissue region.

18. The oximeter sensor of claim 15 wherein at least one of said attachment structure and said members are configured to apply less pressure to said tissue region in a first region between said emitter and said detector than a pressure applied to a second region of said tissue region outside said first region.

19. The oximeter sensor of claim 15 further comprising an adhesive mounted on at least one of said first and second members for securely attaching said sensor to said tissue region.

20. An oximeter sensor comprising:

a light emitter mounted on a first side of a tissue region of a patient;

a light detector mounted on a second side of said tissue region of said patient;

a heating device, mounted proximate at least one of said light emitter and said light detector, said heating device being a thermistor controllable to both heat said patient and also measure the temperature;

an attachment structure configured to attach said sensor to said tissue region so that and said detector is offset from a shortest path through said tissue region from said emitter; and a first diffuse or specular reflective surface mounted to attach to said tissue region in a region of said offset.

21. An oximeter sensor comprising:

a light source mounted on a first side of a tissue region of a patient;

a light collector mounted on said first side of said tissue region of said patient; and a thermistor, mounted proximate at least one of said light source and said light collector, wherein the thermistor is capable of receiving varying current for the purpose of heating said tissue region and measuring the temperature of said tissue region.

22. The oximeter sensor of claim 14 further comprising:

an adhesive for attaching said sensor to said tissue region.

23. The oximeter sensor of claim 22 wherein said thermistor is sufficiently spaced from said light source and light collector so that, when applied to a patient's ear with said adhesive, said light source and light collector are mounted on a side of the ear opposite said thermistor.

24. The oximeter sensor of claim 22 wherein said adhesive is a thermally conductive and electrically isolating layer.

25. The oximeter sensor of claim 22 further comprising a shunt barrier between said light source and said light collector in at least one of said adhesive layer and a substrate connected to said light source and said light collector.

26. The oximeter sensor of claim 25 wherein said shunt barrier comprises a black portion of at least one of said adhesive layer and said substrate.

* * * * *